United States Patent [19]
Lindemann et al.

[11] Patent Number: 6,150,138
[45] Date of Patent: Nov. 21, 2000

[54] EXPRESSION OF A FOAMY VIRUS ENVELOPE PROTEIN

[75] Inventors: Dirk Lindemann, Rimpar; Axel Rethwilm, Würzburg, both of Germany

[73] Assignee: Transgene S.A., Strasbourg, France

[21] Appl. No.: 09/305,086

[22] Filed: May 4, 1999

Related U.S. Application Data

[62] Division of application No. 08/816,439, Mar. 14, 1997, Pat. No. 5,929,222.
[51] Int. Cl.$^7$ .............. C12P 21/04; C07H 21/04; C12N 5/00
[52] U.S. Cl. ............. 435/69.7; 536/23.4; 435/325
[58] Field of Search ................... 435/69.7, 325; 536/23.4

[56] References Cited

PUBLICATIONS

References cited in the parent application were reviewed.

Primary Examiner—Hankyel Park
Attorney, Agent, or Firm—Burns, Doane, Swecker & Mathis, L.L.P.

[57] ABSTRACT

The invention concerns constructs for the expression of a protein comprising at least a modified FV envelope protein, the protein so obtained as well as the complementation cell line permitting the production of pseudotyped viral particle. It also concerns pharmaceutical composition comprising said particles and a method for treating a disease.

12 Claims, 3 Drawing Sheets

HFV wt — Extracellular | Transmembrane | Cytoplasmic
VWPAAASALQGIGNFLSGTAQGIFGTAFSLLGYLKPILIGVGVILLVILIFKIVSWIPTKKKNQ

HFV Δ1

HFV Δ1 MuLV R⁻

HFV Δ1 MuLV

HFV Δ2

HFV Δ2 MuLV R⁻

HFV Δ2 MuLV

HFV SSS

HFV SSS MuLV R⁻

HFV SSS MuLV amino acid 925 930 935 940 945 950 955 960 965 970 975 980 985 990 995 1000 1005 1010 1015 1020

MuLV wt
ETGQGWFEGLFNRSPWFTTLISTIMGPLIVLLLILLFGPCILNRLVQFVKDRISVVQALVLTQQYHQLKPIEYEP

EXPRESSION OF A FOAMY VIRUS ENVELOPE PROTEIN

CROSS REFERENCE TO RELATED APPLICATION

This application is a divisional of U.S. patent application Ser. No. 08/816,439, filed Mar. 14, 1997, now U.S. Pat. No. 5,929,222.

Figure 1:
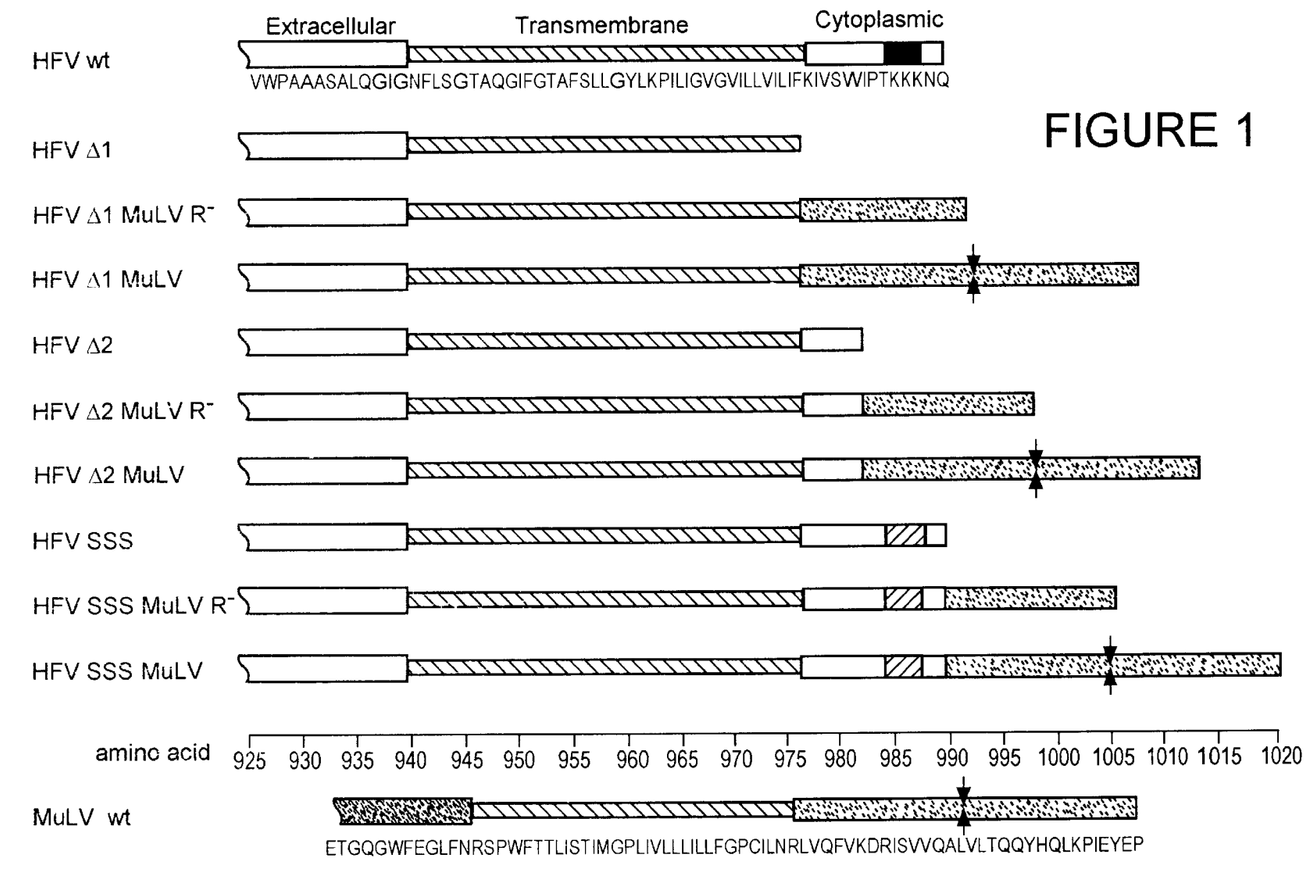

The foamy viruses (FV) subgroup of retroid viruses has attracted scientific interest because of their unique replication strategy and because of their potential use as gene transfer vectors (35). It has been proposed that FVs may be ideal tools for the development of a gene delivery system due to specific properties of this virus group, such as the absence of FV antibodies in the human population, the benign course of natural FV infections, their very broad host cell range, and an extended packaging limit due to the size of the FV genome (4, 30, 32). However, limited knowledge of the molecular biology of this virus group has so far not allowed the development of safe packaging cell lines and vectors, such as those that have been derived for murine retroviruses, among others (27). For instance, the FV genome is a double-stranded DNA with a complex organization. In addition to LTRs (Long Terminal Repeat), a packaging region and gag, pol, env genes, it also comprises several genes such as bel1, bel2, bel3, bet, beo and bes located between env and 3 LTR. The env gene encodes a 130 kDa glycosylated precursor that is cleaved giving rise to the surface (SU) and transmembrane (TM) proteins (see FIG. 1). Furthermore, FVs express their Pol protein from a spliced mRNA independently of the Gag protein, and the mechanism of FV genome packaging and particle assembly, as well as the significance of high amounts of reverse transcribed DNA in the extra-cellular particle are largely unknown (10, 18, 39). Other unique features include the nuclear localization of the Gag precursor protein (31, 40) and the predominant budding into intracytoplasmic vesicles which may be a consequence of the retention of the Env precursor protein in the ER (13).

Moloney retrovirus-based gene transfer vectors are currently the main vehicles for high efficiency stable gene transfer into a wide variety of cell types (20). Major limitations of this vector system are the restricted host-cell range and the inefficient infectivity for some human cells (reviewed in (1)). Recently, several methods using the pseudotyping with foreign envelope proteins, such as the vesicular stomatitis virus (VSV) G glycoprotein (6, 38) or the gibbon ape leukemia virus (GALV) envelope protein (2, 34) have been shown to overcome these disadvantages.

However, the expression of VSV-G for example is highly toxic for the producer cells and has prevented the generation of stable VSV-G packaging cells line (8, 22, 37).

SUMMARY OF THE INVENTION

The invention concerns constructs for the expression of a protein comprising at least a modified FV envelope protein.

The preferred FV according to the present invention is the human foamy virus (HFV), but others may be used (e. g. Simian FV).

The modification may consist in at least a mutation, deletion, substitution and/or addition of one or several amino acid (aa) of said modified FV envelope (env) protein or a combination thereof. Such modification(s) is preferably located into the cytoplasmic tail. Advantageously, a modified FV envelope protein is truncated at aa 975 or, more preferably, 981. The truncation may extend up to the stop codon or alternatively comprise before the stop codon one or several residues optionally from the original FV env protein. Furthermore, a construct of the invention may express a mature modified FV envelope protein or a precursor thereof or a chimeric protein resulting from the fusion of sequences of various origins.

In a particular preferred embodiment, the modified FV env protein in use in the present invention is a fusion protein which furthermore comprises all or preferably a part of a non-FV retroviral envelope protein. Examples of suitable non-FV retroviruses include avian retroviruses, bovine retroviruses, feline retroviruses, murine retroviruses such as Murine Leukemia Virus (MuLV) and particularly Moloney MuLV (MoMuLV), Friend Murine Leukemia (FrMuLV) especially strain FB 29, Murine Sarcoma Virus (MSV), primate retroviruses such as GaLV, VSV or lentiviruses such as HIV (Human Immunodeficiency Virus) or SIV (Simian Immunodeficiency Virus).

In a particularly preferred embodiment, a protein according to the invention consists in HFV protein envelope which all or part of the cytoplasmic domain is replaced by all or part of a cytoplasmic domain of a non-FV retroviral envelope protein, especially of a MuLV envelope protein. Advantageously, the fusion protein consists in the fusion of a MuLV cytoplasmic domain to a modified HFV envelope protein. The MuLV cytoplasmic domain in use in the present invention may be processed or unprocessed. "Processed" means that it contain the cleavage site normally recognized by the corresponding retroviral protease and "unprocessed" that it does not contain it or that it is not functional (mutation, deletion or truncation).

The preferred construct of the invention is the one allowing expression of the fusion protein designated hereinafter HFV Δ2 MuLV.

It is also possible that the construct of the invention is mutated in the donor and/or acceptor splicing sites naturally present in the FV env protein encoding sequence.

The construct of the invention may include regulatory elements to allow transcription and translation of the sequence coding for the modified FV env protein. In particular, a suitable promoter may be linked upstream from the FV env encoding sequence in an operative way by conventional recombinant techniques. Such a promoter may be of prokaryote, eukaryote or viral origin and may be constitutive or regulated. Such regulatory elements are well known in the art.

It is also in the scope of the invention that the construct of the invention may additionally comprise a selection gene enabling detection and isolation of the cells expressing the modified FV env protein. In the context of the invention, the selection gene may be under the transcriptional control of the promoter driving expression of the modified FV env protein resulting in a bicistronic transcript or under the control of an additional promoter region. The possible selection genes are numerous, for example neo gene conferring resistance to antibiotic G418, dihydrofolate reductase (dhFr) gene, puromycin acetyl transferase (pac) gene or xanthine phosphoribosyl transferase (gpt).

The construct of the invention may be inserted in any appropriate vector, a viral vector (e.g. a retroviral vector) or a plasmid. The choice of the appropriate vector is large and within the capabilities of the main skilled in the art. Such a vector may be integrative or not. To decrease the possibility to generate replication-competent viral particles, it is advantageous that the construct lack any retroviral LTR and packaging region.

The invention also concerns fusion proteins as expressed by the above expression constructs as well as pseudotyped viral particles comprising a FV env protein. This latter may be derived from a native FV env protein, a part thereof or a modified one. In a preferred embodiment, the pseudotyped viral particle at its surface comprises a modified FV env protein as expressed by a construct according to the invention. The pseudotyped viral particle of the invention may be generated upon transfection of a recombinant retroviral vector into a complementation cell line. The technology is conventional and described in numerous prior art documents. A retroviral vector in use in the present invention comprises at least a 5' LTR, a packaging region and a 3' LTR derived from any retrovirus such those cited previously and a gene capable of expressing a ribozyme, an anti-sense RNA molecule or a mRNA to further produce a polypeptide of interest. Of particular interest, are therapeutic polypeptides, including but not limited to cytokines (Ile-2, IFN α, β or α). Herpes Simplex Virus type 1 (HSV-1), thymidine kinase (TK), Cystic Fibrosis Transmembrane Conductance Regulator (DFTR), Dystrophin, coagulation Factors (FVIII, FIX, . . . ), tumor associated antigenes (MUC-1, HPV antigenes), antibodies, immunotoxines and anti-HIV drugs.

Another object of the invention is relating to complementation cell line permitting the production of the pseudotyped viral particles and the method of their preparation.

The complementation cell line of the invention may derive from any cell and, particularly, eukaryotic cell. One may envisage murine cell lines, pharmaceutically acceptable cell liens (Vero, CHO, . . . ) or human cell line such as 293. It may be generated by transfection of a construct according to the invention along with a first selection gene. The highest env producer cells are then screened for expression of high levels of FV env protein by immunodetection using antibodies against FV env, Western blot, FACS (Fluorescente Activated Cell Sorter) or any other method. Alternatively the complementation cell line of the invention, may also comprise a construct expressing a retroviral gag/pol gene, more preferably of MuLV, FB 29 or HFV along with a second selection gene different from the first one. Preferably, the env and gag/pol genes are carried by separate expression vector lacking LTR and packaging region. The selection and screening steps are repeated to select a env producing clone which further expresses gag/pol expression product.

A complementation cell line of the invention may be used to package recombinant retroviral vector. The titer may be tested using a conventional retroviral vector expressing a third selection gene different from the previous ones of a masked gene (e.g. Lac Z). As a result, cells producing high titers of pseudotyped viral particles are selected and can be cultured to supply a stable complementation cell line. The cells may also be tested transiently as usually performed and described hereinafter.

According to another aspect of the invention, it is also provided a method for preparing a pseudotyped viral particle of the invention. Such a method comprises the act of (1) introducing a recombinant retroviral vector into a complementation cell line of the invention, (2) culturing said complementation cell line under suitable conditions permitting production of the said pseudotyped viral particle and (3) recovering the resulting pseudotyped viral particle from cell culture.

Preferably, the pseudotyped viral particle is recovered from cell culture supernatant but a cell lysis step may also be considered. The pseudotyped viral particle may also be further purifoied by conventional technology (e.g. ultracentrifugation on sucrose or CICs gradient). Advantageously, the pseudotyped viral particle thus produced is able to infect (preferably in the absence of polybrene) a wide variety of cells and optionally to resist to inactivation by human serum.

According to another aspect of the invention, it is also provided a mammalian host cell infected by the pseudotyped viral particle of the invention. Such a host cell includes without limitation human epithelial, pulmonary, muscular, hepatic, haematopoietic cells, fibroblastes and lymphocytes.

A pseudotyped infectious particle as well as a mammalian cell of the invention may be applied in the prevention or treatment of various diseases, as a vaccine or a therapeutic agent.

It is also the scope of the invention to provide for a pharmaceutical composition comprising a therapeutically or prophylactically effective amount of a pseudotyped viral particle as well as a mammalian cell of the invention as a therapeutic agent. Such a pharmaceutical composition may be produced in a conventional manner. In particular, the particle or the mammalian cell of the invention may be combined with appropriate substances well known in the art, such as a carrier, diluent, adjuvant or excipient. The particular formulation of the pharmaceutical composition depends on various parameters, for example the polypeptide of interest to be expressed, the desired site of action, the method of administration and the subject to be treated. Such a formulation can be determined by those skilled in the art and by conventional knowledge.

In a last embodiment of the invention, it is also provided a method of treating a genetic disorder or a disease induced by any pathogenic gene, such as cancer or a virally-induced disease, which comprises administering a therapeutically effective amount of a pseudotyped viral particle as well as a mammalian cell of the invention to a subject in need of a treatment.

These and other advantages of the subject invention will be apparent from the following example and attached drawings. These embodiments do not represent the full scope of the invention.

In particular, incorporation of human foamy virus (HFV) envelope proteins into murine leukemia virus (MuLV) particles was studied in a transient transfection packaging cell system. We report here that wildtype HFV envelope protein can pseudotype MuLV particles, albeit at low efficiency. Complete or partial removal of the HFV cytoplasmic tail resulted in an abolishment or reduction of HFV mediated infectivity, implicating a role of the HFV envelope cytoplasmic tail in the pseudotyping of MuLV particles. Mutation of the ER retention signal present in the HFV envelope cytoplasmic tail did not result in a higher relative infectivity of pseudotyped retroviral vectors. However, a chimeric envelope protein, containing an unprocessed MuLV envelope cytoplasmic domain fused to a truncated HFV envelope protein, showed an enhanced HFV specific infectivity as a result of an increased incorporation of chimeric envelope proteins into MuLV particles.

BRIEF DESCRIPTION OF THE DRAWINGS

FIG. 1

Schematic illustration of the HFV envelope expression constructs.

The extracellular, membrane spanning, and cytoplasmic domains of the TM components of the HFV (open boxes) and the MuLV (shaded boxes) envelopes are shown according to (11, 24). The amino acid sequence of the wildtype HFV and MuLV proteins are given below the schematic illustration. The amino acid positions in the HFV envelope constructs are marked on the ruler. The location of the sequence motif in the cytoplasmic domain of the HFV envelope, responsible for ER retention (13) is indicated as a black box, the mutated sequence as a striped box. The cleavage site of the MuLV protease in the full length cytoplasmic domain of the MuLV envelope protein is indicated by two inverted arrows.

FIG. 2

Infectivity of MuLV particles pseudotyped with different envelope proteins.

NIH3T3 (shaded bar) or QT-6 (solid bar) cells were infected with different pseudotyped MuLV particles generated by transient transfection of 293T cells. Forty-eight hours after transduction the percentage of GFP expressing cells was quantitated by FACS analysis. The mean fluorescence of GFP expressing cells was 100 to 300 fold above those of mock infected cells. The individual envelope constructs used for pseudotyping are indicated on the y-axis of the graph. The mean percentage of GFP expressing cells for each construct is shown on the x-axis with the corresponding standard deviation. Individual constructs were tested 2–6 times.

FIG. 3

Neutralization of HFV envelope specific infectivity.

MuLV particles pseudotyped with different envelope proteins, as indicated on the y-axis, were generated by transient transfection of 293T cells. Supernatants (1 ml) were incubated with anti-HFV specific chimpanzee serum (1:60) (solid bar) or human serum (1:60) from a healthy individual (shaded bar) for 1 hour at 37° C. prior to the addition to NIH3T3 (A) or QT-6 (B) cells. The supernatant was aspirated four hours later, and replaced with fresh growth medium. Forty eight hours after transduction, the percentage of GFP expressing cells was determined as described in the legend of FIG. 2. The experiment was carried out twice with a neutralizing monkey serum and in addition, with an anti-HFV surface rabbit serum (data not shown) resulting in a similar relative inhibition of the infectivity of HFV envelope pseudotyped retroviral vectors.

The present invention will now be illustrated in the following and non limiting example.

EXAMPLE

All constructions are made by using standard recombinant DNA techniques such as those described in T. Maniatis et al., Molecular cloning: a laboratory manual, Cold Spring Harbor, N.Y. 1982. The cell lines are accessible by the culture collections such as ATCC and cultured by standard conditions (NIH3T3:CRL-1658, Mv.1.Lu CCL64, HT 1080 CCL 121, BHK 21 CCL 10, QT 26 CRL 1708 and 293 CRL 1573). The sequence of the HFV env protein has already been published.

1. Generation of FV env expression construct

An eukaryotic expression construct for the envelope gene of the human FV isolate (HFV) was generated by inserting a 3076 bp AflIII/EcoRI fragment of the HFV proviral clone pHSRV1 (28), containing the full-length env open reading frame (ORF), into the pCDNA3 (Invitrogen) vector. This construct was designated pCHFV wt and used to generate the mutant and chimeric HFV envelope proteins depicted in FIG. 1. Briefly, truncated or chimeric env constructs were made by using the polymerase chain reaction on HFV and/or MuLV env genes as templates and oligonucleotides incorporating the desired mutations. The mutants were inserted into the basic vector described above and sequenced to exclude off-site mutations. Three mutant HFV envelope constructs were generated. pCHFV Δ1 and pCHFV Δ2 code for HFV envelope proteins truncated at as 975 or 981, respectively. pCHFV Δ2 has a c-terminal Arginine added, not present in the original HFV env sequence. According to the HFV envelope domain structure proposed by Flugel et al. (11) the truncations resulted in a complete (pCHFV) Δ1) or partial removal (pCHFV Δ2) of the cytoplasmic domain. Finally, the pCHFV SSS construct produces an HFV envelope protein that has the triple lysine motif (aa 984–986) at the C-terminal end of the cytoplasmic tail of the transmembrane (TM) protein replaced by the serine residues. This sequence motif has been shown to be responsible for the ER retention of the HFV envelope (13, 14).

The total 6 chimeric envelope proteins were constructed by C-terminal fusion of sequences coding for the unprocessed or processed cytoplasmic domain of the MuLV envelope protein (16, 17). pCHFV Δ1MuLVR-, pCHFV Δ2 MuLVR- and pCHFV SSSMuLVR-encode fusion proteins consisting of the 3 mutations described above and a processed MuLV envelope cytoplasmic domain (aa 634–649), whereas pCHFV Δ1MuLV, pCHFV Δ2MuLV and pCHFV SSSMuLV encode the respective fusion proteins containing an unprocessed MuLV envelope cytoplasmic domain (aa 634–665) as the c-terminus.

The expression constructs for the MuLV gag/pol (pHIT60), the ecotropic (pHIT123) and amphotropic (pHIT456) MuLV envelope were kindly provided by A. Kingsman (33). The retroviral vector SFG GFPS65T contains the humanized ORF of the green fluorescent protein (7) (a gift of M. Vogel) inserted into the cloning sites of the MuLV based retroviral vector SFG (5, 22), whereas MFG.S NLS-LacZ (22) contains the β-galactosidase gene fused to the SV40 nuclear localization signal (NLS) (a gift of R. Mulligan). The VSV-G expression construct was generated by inserting a 1.6 kg EcoRI fragment from plasmid pSVGL-1 (29) (a gift of J. Rose) containing the VSV-G ORF, into the pHIT vector.

2. Infectivity of MuLV particles pseudotyped with various HFV env proteins

Recombinant retroviral particles were generated using the pHIT packaging system essentially as described previously (33). Briefly, 293T cells (9) were transiently co-transfected with an expression construct for MuLV gag/pol (pHIT60), the MuLV based retroviral vector SFG GFPS65T, and the different envelope expression constructs described above. Viral supernatants were harvested 48–72 hours after transfection. Supernatants from independent transfections with the same plasmids were pooled, filtrated (0.45 μm pore size), polybrene was added to a final concentration of 8 μg/ml, and the supernatants were used immediately or stored at −80° C. until use. Target cells expressing the GFP protein after retroviral transduction were identified by FACS analysis on a FACScan, and the number of positive cells were quantitated using the LysisII and CellQuest Software package (Becton Dickinson).

Figure 2:
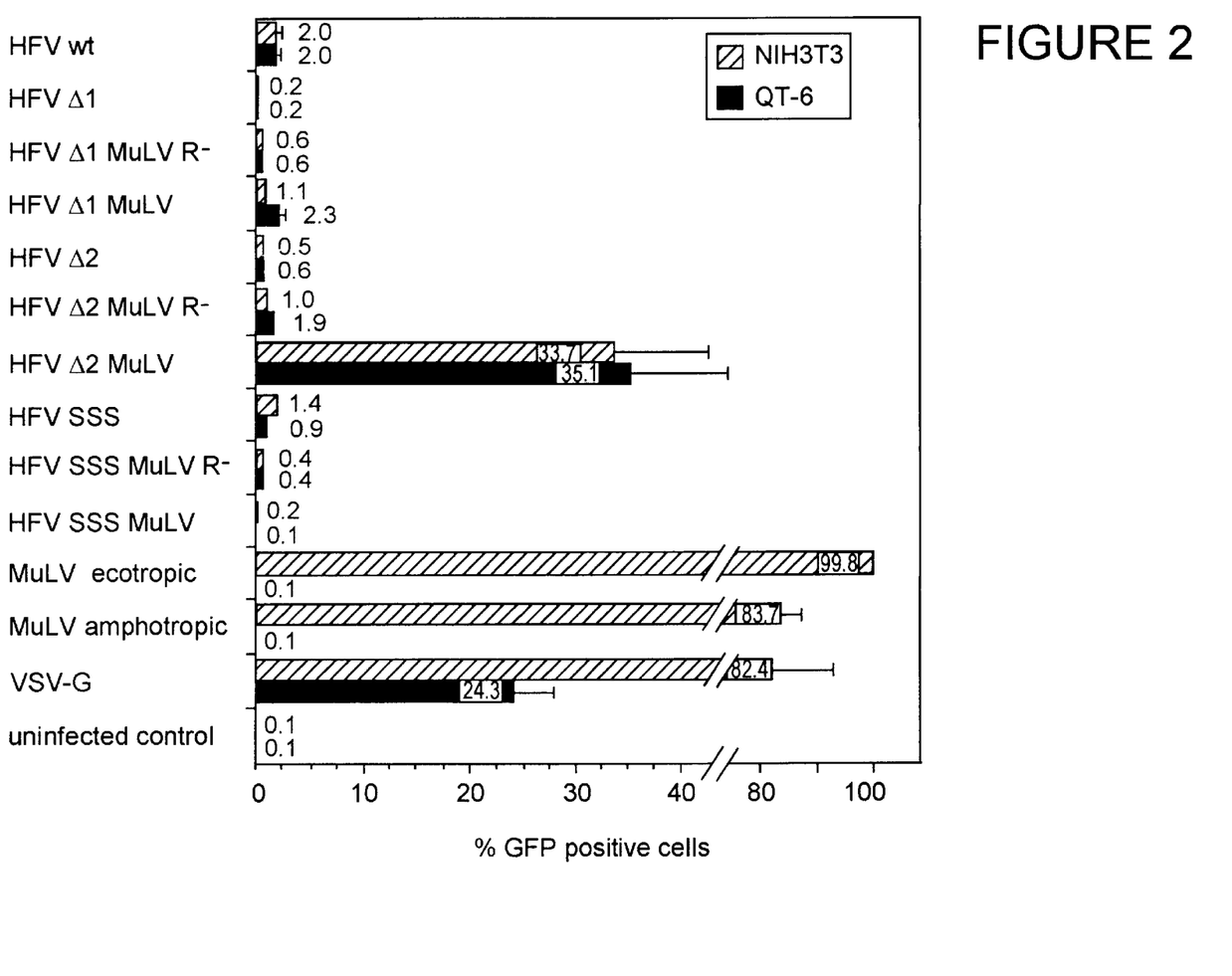
Figure 3A:
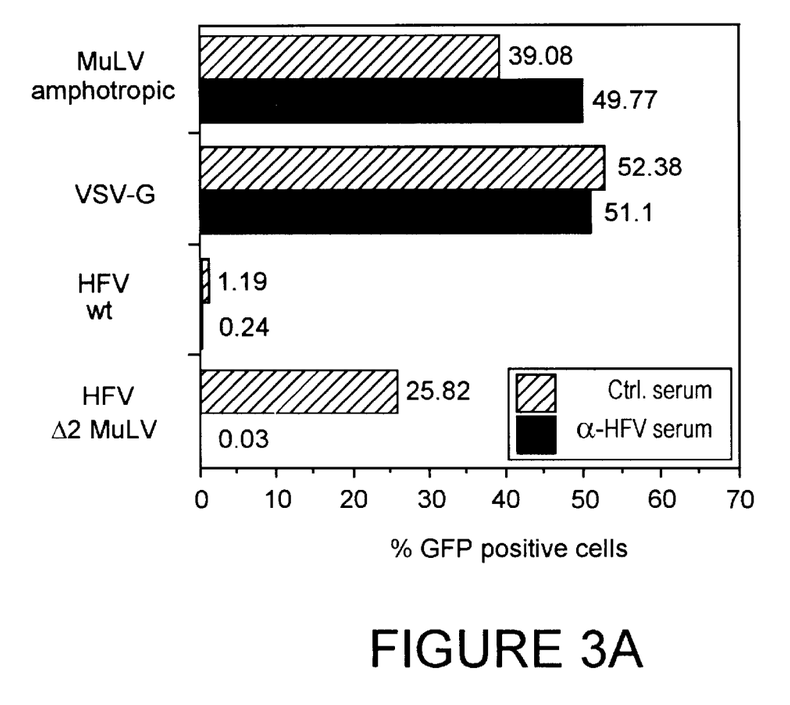
Figure 3B:
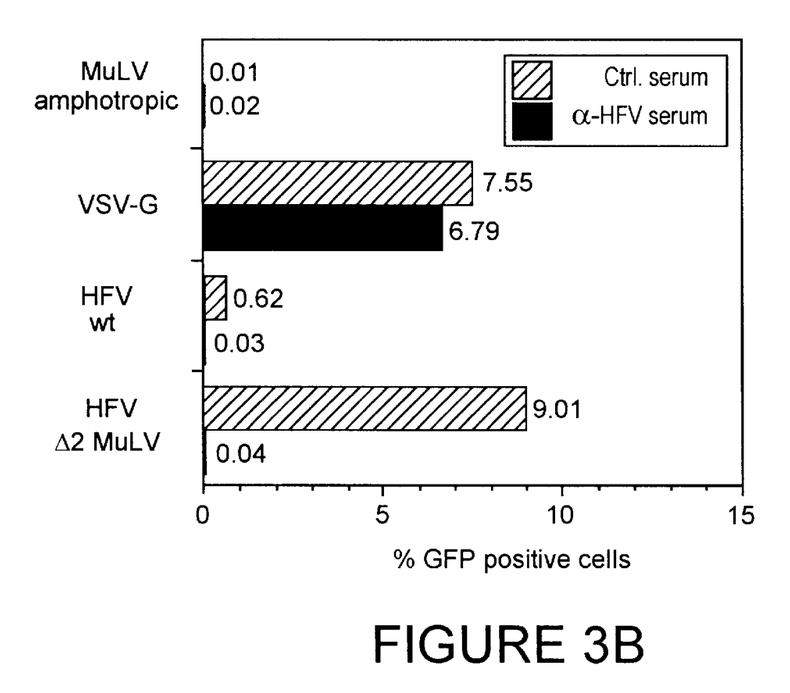

Initial experiments using the pCHFV wt expression construct showed that MuLV particles can be pseudotyped with the HFV wt envelope protein and are able to transduce NIH3T3 cells, albeit at low efficiency (FIG. 2). The HFV envelope protein contains a signal sequence in its cytoplasmic domain that leads to a retention in the ER of expressing cells (13, 14). Therefore, three constructs, pCHFV Δ1, pCHFV Δ2, and pCHFV SSS, coding for cytoplasmically truncated or mutated HFV envelope proteins were examined to determine the influence of the cytoplasmic domain of the HFV envelope and its ER retention on the pseudotyping efficiency. The complete (pCHFV Δ1) or partial removal (pCHFV Δ2) of the cytoplasmic domain of the HFV envelope results in an abolishment or reduction of the already low pseudotyping activity observed for the wildtype protein (FIG. 2). Mutation of the cytoplasmic ER retention signal (pCHFV SSS) has previously been shown to increase cell surface expression of the HFV envelope protein (13). However, pseudotyping of viral particles with such a mutant protein also did not result in higher infectivity of these viruses (FIG. 2).

Since removal or modification of the HFV cytoplasmic domain failed to increase the infection efficiency of pseudotyped virus, a second approach has subsequently been used to test whether the replacement of the HFV cytoplasmic domain by the MuLV cytoplasmic domain, or the fusion of the MuLV cytoplasmic domain to a modified full-length HFV envelope would have the desired effect. The cytoplasmic domain of the MuLV envelope was shown to be processed by the MuLV protease in the viral particle (16, 17). Expression of an already processed form of the MuLV envelope protein in cells resulted in the formation of large multinucleated syncytia and a decrease of viral infectivity (24, 26). Therefore, C-terminal fusion proteins of the three mutants described above and the processed (MuLVR-) or the unprocessed (MuLV) cytoplasmic domain of the MuLV envelope protein were generated and particles pseudotyped with these chimeric envelope proteins were tested for their infectivity on NIH3T3 cells. Interestingly, viruses pseudotyped with one mutant, the HFV Δ2MuLV protein, showed a 10–20 fold higher infectivity than particles pseudotyped with the wildtype HFV envelope protein (FIG. 2). This increase in infectivity through the HFV Δ2MuLV protein was not specific for NIH3T3 or murine cells, as similar results were obtained for the quail fibroblast cell line QT-6, which is not infectable by viral particles coated with MuLV envelope proteins (FIG. 2). In these cells the infectivity of particles pseudotyped with the HFV Δ2MuLV envelope protein was consistently higher than those pseudotyped with the VSV-G protein. All other proteins analyzed gave rise to pseudotyped viruses with lower or similar relative infectivity when compared to wildtype HFV envelope on both cell lines (FIG. 2). In addition, chimeric HFV envelope proteins containing a processed MuLV cytoplasmic domain showed a higher fusion activity than the corresponding proteins having an unprocessed MuLV cytoplasmic domain upon expression in L929 cells by retroviral vectors (data not shown). This result is in accordance with data showing that the cytoplasmic domain of the MuLV envelope can control the fusion activity of foreign envelope proteins, such as the simian immunodeficiency virus (SIV), when expressed as a chimeric envelope protein (36). Furthermore, supernatants containing a retroviral vector coding for a nuclear localized β-galactosidase protein pseudotyped with the different envelope proteins were titrated on cell lines of various species (Table). More precisely, target cells ($1\times10^4$ cells/well) were plated 24 hours prior to infection with serial dilutions of supernatants of truncated 293T cells. Fourtyeight hours after infection the numbers of blue foci were counted in duplicates and the titers calculated. The values of the duplicates were within a 3-fold range. The results shown are a representative of two independent titrations on the cell lines indicated using for all cell lines cell free supernatants from the same transfections, with reproducible relative titers in both experiments. Supernatants containing pseudotyped particles were titrated up to 6 times on NIH3T3 cells with reproducible results. Retroviral particles pseudotyped with the HFV wt envelope protein or the HFV Δ2MuLV chimera were able to infect cells of human, mink and hamster origin, in addition to murine cells (Table). The titers of retroviral vectors pseudotyped with the HFV Δ2MuLV envelope protein were 8–35 fold higher than those pseudotyped with the wildtype HFV envelope protein depending on the target cells used.

TABLE

Viral titers of retroviral vectors pseudotyped with different envelope proteins on various cell lines

| Envelope | Virus titer (no. of blue foci/ml) NIH3T3 | L929 | Mv.1.Lu | HT1080 | BHK-21 | QT-6 |
|---|---|---|---|---|---|---|
| MuLv ecotropic | $1.1 \times 10^6$ | $1.3 \times 10^5$ | <10 | <10 | $5.0 \times 10^2$ | <10 |
| MuLV amphotropic | $1.6 \times 10^6$ | $5.4 \times 10^5$ | $4.1 \times 10^5$ | $3.3 \times 10^5$ | $2.4 \times 10^2$ | <10 |
| VSV-G | $4.3 \times 10^4$ | $4.7 \times 10^4$ | $3.2 \times 10^4$ | $9.2 \times 10^3$ | $4.3 \times 10^4$ | $3.9 \times 10^3$ |
| HFV wt | $3.0 \times 10^3$ | $2.4 \times 10^2$ | $7.1 \times 10^2$ | $3.0 \times 10^2$ | $2.5 \times 10^2$ | $1.5 \times 10^2$ |
| HFV Δ2 MuLv | $3.3 \times 10^4$ | $2.0 \times 10^3$ | $1.1 \times 10^4$ | $3.2 \times 10^3$ | $7.3 \times 10^3$ | $5.5 \times 10^3$ |

3. Neutralization of the infectivity of HFV env pseudotyped particles by HFV specific antisera To confirm that the infectivity of MuLV particles pseudotyped with different HFV envelope proteins was specific for the HFV envelope, pseudotyped particles were preincubated with an anti-HFV specific chimpanzee serum prior to the addition to target cells (3). The infectivity of viral particles pseudotyped with the amphotropic MuLV envelope or the VSV-G protein was not reduced by preincubation with the HFV specific antiserum when compared to the preincubation of these viruses with normal heat inactivated human serum (FIG. 3) or mock incubated viral particles (data not shown). In contrast, the infectivity of particles pseudotyped with the wildtype HFV envelope protein or the HFV Δ2MuLV chimera was completely abolished by the preincubation with the HFV specific antiserum but not the human control serum (FIG. 3). This neutralization of the HFV envelope specific infectivity was observed for NIH3T3 (FIG. 3A) and QT-6 (FIG. 3B) cells. A similar specific neutralization of viral particles pseudotyped with HFV envelope proteins was obtained in experiments using a rabbit serum raised against the baculovirus expressed SU domain of the HFV envelope protein (data not shown).

4. Expression and particle incorporation of HFV env proteins

The expression and incorporation of the different HFV envelope proteins into MuLV particles was determined by radioimmunoprecipitation analysis (RIPA) of transiently transfected 293T cells. Forty-eight hours after addition of the DNA (pHIT60, SFG GFPS65T and various env constructs), cells were metabolically labeled with [$^{35}$S] methionine for approximately 20 h. Viral particles present in the supernatant were pelleted by centrifugation at 25,000 rpm through a 20% sucrose cushion prior to solubilization in lysis buffer. Subsequently, the samples were submitted to immunoprecipitation. Immunoprecipitates of the viral particles with an HFV specific chimpanzee serum or antiMuLV gag hybridoma supernatants were analyzed by SDS-polyacrylamide gel electrophoresis (PAGE) along with their corresponding cell lysates. HFV specific bands in immunoprecipitates from pelleted virus or cellular lysates were only observed in samples transfected with the HFV env expression constructs, but not in samples expressing the MuLV amphotropic envelope protein or mock transfected cultures. Two predominant HFV envelope precursor bands of 130 and 110 KD were observed in immunoprecipitates of cellular lysates of HFV env transfected cells (12, 21). In addition, two bands corresponding to the processed −90 KD SU and the −45–50 KD TM proteins could be observed after longer exposure. The different apparent sizes of the TM proteins in the cellular samples transfected with the various HFV mutants reflected the modifications in the TM portion of the individual proteins. Only moderate differences in the steady state level of the different envelope proteins in the transfected cells were observed, except for the HFV SSSMuLVR- and the HFV SSSMuLV proteins which showed a clearly reduced cellular expression. Both envelope precursor proteins as well as the processed SU and TM proteins were also detected in immunoprecipitates of pelleted viral particles. However, in general the relative ratio of processed proteins to precursor proteins was increased in the viral particle immunoprecipitates compared to the cell lysates.

Interestingly, a good correlation between the amount of processed SU and TM proteins in the individual immunoprecipitates of the viral particles and the relative infectivity of the corresponding pseudotyped particles (FIG. 2) could be observed. The HFV Δ2MuLV chimeric envelope, which gave rise to pseudotyped particles with the highest relative infectivity also showed the strongest SU and TM bands in the RIPA. The amount of MuLV gag/pol proteins in the individual viral particle preparations, as determined in crude viral pellets or immunoprecipitates with anti-gag hybridoma supernatants, was similar for all samples, except for the HFV Δ2MuLV envelope transfection. This sample showed a significant decrease in particle associated gag/pol proteins, indicating that fewer MuLV particles were present in this preparation compared to the other viral pellets. As a result, the relative amount of processed HFV SU and TM proteins per individual viral particle may be even higher than estimated from the immunoprecipitates of viral particles preparations with HFV specific antibodies. A possible explanation for this phenomenon is an enhanced absorbance of these particles by transfected cells not expressing the HFV env protein, as a result of the increased infectivity of HFV Δ2MuLV pseudotyped particles compared to particles pseudotyped by the other HFV envelope proteins. This may result in a clearing of the HFV Δ2MuLV pseudotyped particles from the supernatant. Furthermore, in contrast to MuLV particles pseudotyped with amphotropic MuLV envelope or VSV-G, HFV pseudotyped viruses showed no reduction in infectivity in the absence of polycations such as polybrene (30). Therefore, the relative titers of retroviral vectors pseudotyped with HFV envelope by transient transfection may be underestimated compared to pseudotypes with amphotropic MuLV envelope or VSV-G. Further experiments, however, using cell lines stably expressing the HFV envelope, which should be resistant to infection by viruses pseudotyped with the HFV envelope, are necessary to clarify these phenomena in more detail.

5. Inactivation of the splice donor and acceptor sites located into the FV env gene Furthermore, Bel-1 and Bet transcripts derived from internal HFV promoter (Pos. 8419 relative to the transcription start in the 5' LTR), located within the HFV envelope ORF (Pos. 6310–9276) efficiently utilize a splice donor (SD, Pos. 9119 and a splice acceptor (SA, Pos. 9237) site within the coding region of TM subunit of the env protein. Alternative splicing of mRNA coding for the HFV env protein utilizing these SD and SA sites results in potential envelope/bel fusion proteins. A ~170 KD can be detected in HFV infected cells by immunoprecipitation and the mRNA is detectable by RT (reverse-transcriptase) PCR of total mRNA from HFV infected human fibroblasts. Inactivation of the SD (Pos. 9119) by a GT→GG mutation results in a disapearance of the 170 KD envelope fusion protein, while the expression of the 130 KD envelope precursor protein is not changed. The biological function of the env/bel fusion proteins as well as the influence on viral titers of pseudotyped MuLV particles are currently not known. Preliminary experiments using the GFP expression MuLV retroviral vectors are described above indicate no influence on the relative infectivity.

In summary, a system has been generated to produce MuLV based retroviral vectors pseudotyped with HFV envelope proteins. The cytoplasmic domain of the HFV envelope protein was at least partially involved in pseudotyping of MuLV particles as progressive deletion of the cytoplasmic domain lead to a reduction in gene transfer and incorporation of HFV env SU and TM subunits into the viral particle. Addition of an unprocessed MuLV envelope cytoplasmic domain to one deletion mutant, the HFV Δ2MuLV envelope, resulted in a 10–20 fold increase in infectivity compared to HFV wildtype envelope protein and an enhanced incorporation of the chimeric envelope protein into pseudotyped particles. Retroviral titers were 8–35 fold higher than those achieved by pseudotyping with the wildtype HFV envelope protein. On some target cell types, the gene transfer efficiency was similar or higher than those of retroviral vectors pseudotyped with the VSV-G protein. In the case of the wildtype MuLV envelope protein, the role of the cytoplasmic domain for the specific incorporation of the envelope into the viral particles is unclear. Some cytoplasmic tail deletion mutants resulted in a loss of particle associated envelope proteins (15), whereas other mutant envelope proteins showed little or no reduction in particle association (25, 26). Our results argue for a role of the MuLV env cytoplasmic domain in the particle association of the envelope protein, at least in the enhanced incorporation of chimeric envelope proteins into MuLV particles.

Recently, the pseudotyping of MuLV based retroviral vectors with foreign envelope proteins, such as the VSV glycoprotein G (6, 38) or the GALV envelope (2, 34), has resulted in an increase in virus stability, a broadened host-cell range and an enhanced transduction efficiency of certain cell types. The broad host range of FVs, the resistance to inactivation by human serum (30), and the efficient infection of cells of various origin in the absence of polycations (unpublished observations and (30)) should make MuLV based retroviral vectors pseudotyped with the HFV Δ2MuLV chimeric envelope protein a useful new tool for efficient gene transfer into different cell types. Unlike the expression of VSV-G, which is highly toxic for the producer cells and has prevented the generation of stable VSV-G packaging cell lines until recently (8, 22, 37), transient expression of the HFV Δ2MuLV envelope resulted in no apparent toxicity in 293T cells (data not shown, (19)).

REFERENCES

1/ Adams, R. M., H. E. Soriano, M. Wang, G. Darlington, D. Steffen, and F. D. Ledley. 1992. Transduction of primary human hepatocytes with amphotropic and xenotropic retroviral vectors. Proc Natl Acad Sci USA 89:8981–5.

2/ Bauer, T., Jr., A. D. Miller, and D. D. Hickstein. 1995. Improved transfer of the leukocyte integrin CD18 subunit into hematopoietic cell lines by using retroviral vectors having a gibbon ape leukemia virus envelope. Blood 86: 2379–87.

3/ Bieniasz, P. D., A. Rethwilm, R. Pitman, M. D. Daniel, I. Chrystie, and M. O. McClure. 1995. A comparative study of higher primate foamy viruses, including a new virus from a gorilla. Virology 207: 217–28.

4/ Bieniasz, P. D., R. A. Weiss, and M. O. McClure. 1995. Cell cycle dependence of foamy retrovirus infection. J. Virol. 69: 7295–7299.

5/ Bueler, H., and R. C. Mulligan. 1996. Induction of antigen-specific tumor immunity by genetic and cellular vaccines against MAGE: enhanced tumor protection by coexpression of granulocyte-macrophage colony-stimulating factor and V7-1. Mol. Med. 2: 545–555.

6/ Burns, J. C., T. Friedmann, W. Driever, M. Burrascano, and J. K. Yee. 1993. Vesicular stomatitis virus G glycoprotein pseudotyped retroviral vectors: concentration to very high titer and efficient gene transfer into mammalian and nonmammalian cells. Proc Natl Acad Sci USA 90: 8033–7.

7/ Chalfie, M., Y. Tu, G. Euskirchen, W. W. Ward, and D. C. Prasher. 1994. Green fluorescent protein as a marker for gene expression Science 263: 802–5.

8/ Chen, S. T., A. Iida, L. Guo, T. Friedmann, and J. K. Yee. 1996. Generation of packaging cell lines for pseudotyped retroviral vectors of the G protein of vesicular stomatitis virus by using a modified tetracycline inducible system. Proc Natl Acad Sciences USA 93:10057–10062.

9/ Du Bridge, R. B., P. Tang, H. C. Hsia, P. M. Leong, J. H. Miller, and M. P. Calos. 1987. Analysis of mutation in human cells by using an Epstein-Barr virus shuttle system. Mol Cell Biol 7: 37987.

10/ Enssle, J., I. Jordan, B. Mauer, and A. Rethwilm. 1996. Foamy virus reverse transcriptase is expressed independently from the gag protein, Proc Natl. Acad. Sci. (USA) 93: 4137–4141.

11/ Flügel, R. M., A. Rethwilm, B. Maurer, and G. Darai. 1987. Nucleotide sequence analysis of the env gene and its flanking regions of the human spumaretrovirus reveals two novel genes EMBO 6: 2077–2084.

12/ Giron, M. L., F. Rozain, M. C. Debons-Guillemin, M. Canivet, J. Peries, and R. Emanoil-Ravier. 1993. Human foamy virus polypeptides: identification of env and bel gene products J. Virol 67: 3596–600.

13/ Goepiert, P. A., K. L. Shaw, G. D. J. Ritter, and M. J. Mulligan. 1996. A sorting motif localizes the foamy virus glycoprotein to the endoplasmic reticulum. J. Virol. 71: 778–784.

14/ Goepfert, P. A., G. Want, and M. J. Mulligan. 1995. Identification of an ER retrieval signal in a retroviral glycoprotein. Cell 82: 543–544.

15/ Granowitz, C., J. Colicelli, and S. P. Goff. 1991. Analysis of mutations in the envelope gene of Moloney Murine Leukemia Virus: Separation of infectivity from superinfections Resistance. Virology 183: 545–554.

16/ Green, N., T. M. Shinnick, O. Witte, A. Ponticelli, J. G. Sutcliffe, and R. A. Lerner. 1981. Sequence-specific antibodies show that maturation of Moloney leukemia virus envelope polyprotein involves removal of a COOH terminal peptide. Proc. Natl. Acad. Sci. USA 78: 6023–6027.

17/ Henderson, L. E., R. Sowder, T. D. Copeland, G. Smythers, and S. Oroszian. 1984. Quantitative separation of murein leukemia virus proteins by reversed-phase high pressure liquid chromatography reveals newly described gag and env cleavage products. J. Virol. 52:492–500.

18/ Jordan, I., J. Enssle, E. Guttler, B. Mauer, and A. Rethwilm. 1996. Expression of human foamy virus reverse transciptase involves a spliced pol mRNA. Virology 224: 314–319.

19/ Mikovits, J. A., P. M. Hoffman, A. Rethwilm, and F. W. Ruscetti. 1996. In vitro infection of primary and retroviral infected human leukocytes by human foamy virus. J. Virol. 70: 2774–2780.

20/ Miller, A. D. 1992 Human gene therapy comes of age. Nature 357: 455–60.

21/ Netzer, K. O., A. Rethwilm, B. Maurer, and V. ter Meulen. 1990. Identification of the major immunogenic structural proteins of human foamy virus. J Gen Virol. 71: 1237–41.

22/ Ory, D. S., B. A. Neugeboren, and R. C. Mulligan. 1996 A stable human-derived packaging cell line for production of high titer retrovirus/vesicular stomatitis virus G pseudotypes. Proc. Natl Acad Sciences USA 93: 11400–11406.

23/ Owens, R. J., and K. Rose. 1993. Cytoplasmic domain requirement for incorporation of a foreign envelope protein into vesicular stomatis virus. J. Virol. 67: 360–5.

24/ Ragheb, J. A., and W. F. Anderson. 1994. pH-independent Murine Leukemia Virus ecotropic envelope-mediated cell fusion: Implications for the role of the R peptide and p12E TM in viral entry. J. Virol. 68: 3220–3231.

25/ Ragheb, J. A., and W. F. Anderson. 1994. Uncoupled expression of Moloney Murine Leukemia Virus envelope polypeptides SU and TM: a functional analysis of the role of TM domains in viral entry. J. Virol. 68: 3207–3219.

26/ Rein, A., A. Mirro, J. Gordon Haynes, S. M. Ernst, and K. Nagashima. 1994. Function of the cytoplasmic domain of a retroviral transmembrane protein: p15E-p2E cleavage activates the membrane fusion capability of the Murine Leukemia Virus env protein. J. Virol. 68: 1773–1781.

27/ Rethwilm, A. 1996. Unexpected replication pathways of foamy viruses. J. Acquired Immune Defic. Syndr. Hum. Retrovirol.

28/ Rethwilm, A., G. Baunach, K. O. Netzer, B. Maurer, B. Borisch, and V. T. Meulen. 1990. Infectious DNA of the human spumaretrovirus. Nucleic Acids Res. 18: 733–738.

29/ Rose, J. K., and J. E. Bergmann. 1983. Altered cytoplasmic domains affect intracellular transport of the vesicular stomatitis virus glycoprotein. Cell 34: 513–524.

30/ Russell, D. W., and A. D. Miller. 1996. Foamy virus vectors. J. Virol. 70: 217–222.

31/ Schliephake, A. W., and A. Rethwilm. 1994. Nuclear localization of foamy virus gag precursor protein. J. Virol. 68: 4946–4954.

32/ Schmidt, M., and A. Rethsilm. 1995. Replicating foamy virus-based vectors directing high level expression of foreign genes. Virology 210: 167–78.

33/ Soneoka, Y., P. M. Cannon, E. E. Ransdale, J. C. Griffiths, G. Romano, S. M. Ringsman, and A. J. Kingsman. 1995. A transient three-plasmid expression system for the production of high titer retroviral vectors. Nucleic Acids Res 23: 628–33.

34/ von Kalle, C., H. P. Kiem, S. Goehle. B. Darovsky, S. Heinfeld, B. Torok-Storb, R. Storb, and F. G. Schuening. 1994. Increased gene transfer into human hematopoietic progenitor cells by extended in vitro exposure to a pseudotyped retroviral vector. Blood 84: 2890–7.

35/ Weiss, R. A. 1996. Foamy viruses bubble on. Nature 380: 201.

36/ Yang, C., and R. W. Compans, 1996. Analysis of the cell fusion activities of chimeric simian immunodeficiency virus-murine leukemia virus envelope proteins: inhibitory effects of the R peptide. J. Virol. 70: 248–254.

37/ Yang, Y., E. F. Vanin, M. A. Whitt, M. Fornerod, R. Zwart, R. D. Schneiderman, G. Growveld, and A. W. Nienhuis. 1995. Inducible, high-level production of infectious murine leukemia retroviral vector particles pseudotyped with vesicular stomatitis virus G envelope protein. Hum Gene Ther 6: 1203–13.

38/ Yee, J. K., A. Miyanohara, P. LaPorte, K. Bouic, J. C. Burns, and T. Friedmann. 1994. A general method for the generation of high-titer, pantropic retroviral vectors. Highly efficient infection of primary hepatocytes Proc Natl Acad Sciences USA 91: 9564–9568.

39/ Yu, S. F., D. N. Baldwin, S. R. Gwynn, S. Yendapalli, and M. L. Linial. 1996. Human foamy virus replication: a pathway distinct from that of retroviruses and hepadnaviruses. Science 271: 15791582.

40/ Yu, S. F., K. Edelmann, R. K. Strong. A Moebes, A. Rethwilm, and M. L. Linial. 1996. The carboxyl terminus of the human foamy virus gag protein contains separable nucleic acid binding and nuclear transport domains. J. Virol. 70: 8355–8262.

What is claimed is:

1. A pseudotyped viral particle comprising a protein expressed by a vector, wherein said protein comprises a functional, modified foamy virus (FV) envelope protein.

2. A method for the preparation of the pseudotyped viral particle according to claim 1, which comprises:
   (i) introducing a recombinant retroviral vector into a complementation cell,
   (ii) culturing said complementation cell line under suitable conditions to permit the production of the said pseudotyped viral particle, and
   (iii) recovering said pseudotyped viral particle in the cell culture.

3. A isolated mammalian cell infected with a pseudotyped viral particle according to claim 1.

4. A isolated mammalian cell infected with a pseudotyped viral particle obtainable by a method according to claim 2.

5. A pharmaceutical composition comprising a therapeutically or prophylactically effective amount of a pseudotyped viral particle according to claim 1.

6. A pharmaceutical composition comprising a therapeutically or prophylactically effective amount of a pseudotyped viral particle obtainable by a method according to claim 2.

7. A pharmaceutical composition comprising a therapeutically or prophylactically effective amount of a pseudotyped viral particle obtained from a mammalian cell according to claim 3.

8. A pharmaceutical composition comprising a therapeutically or prophylactically effective amount of a pseudotyped viral particle obtained from a mammalian cell according to claim 4.

9. A method for treating a disease which comprises administering a therapeutically effective amount of a pseudotyped viral particle according to claim 1.

10. A method for treating a disease which comprises administering a therapeutically effective amount of a pseudotyped viral particle obtainable by a method according to claim 2.

11. A method for treating a disease which comprises administering a therapeutically effective amount of a pseudotyped viral particle obtained from a mammalian cell according to claim 3.

12. A method for treating a disease which comprises administering a therapeutically effective amount of a pseudotyped viral particle obtained from a mammalian cell according to claim 4.

* * * * *